(12) United States Patent
Toyama (10) Patent No.: US 7,939,299 B2
(45) Date of Patent: May 10, 2011

(54) NUCLEIC ACID AMPLIFICATION METHOD (75) Inventor: Masafumi Toyama, Yokohama (JP)

(73) Assignee: Toyo Seikan Kaisha, Ltd., Tokyo (JP)

( * ) Notice: Subject to any disclaimer, the term of this patent is extended or adjusted under 35 U.S.C. 154(b) by 0 days.

(21) Appl. No.: 12/439,155

(22) PCT Filed: Aug. 31, 2007

(86) PCT No.: PCT/JP2007/066979
§ 371 (c)(1),
(2), (4) Date: Feb. 26, 2009

(87) PCT Pub. No.: WO2008/026719
PCT Pub. Date: Mar. 6, 2008

(65) Prior Publication Data
US 2010/0015617 A1    Jan. 21, 2010

(30) Foreign Application Priority Data
Aug. 31, 2006  (JP) ................. 2006-235838
Sep. 21, 2006  (JP) ................. 2006-255525

(51) Int. Cl.
*C12P 19/34*    (2006.01)
*C12Q 1/68*    (2006.01)
*C07H 21/00*    (2006.01)

(52) U.S. Cl. ......... 435/91.1; 435/91.2; 435/6; 536/23.1; 536/24.3; 536/24.33; 422/61

(58) Field of Classification Search ............. 435/6, 91.1, 435/91.2; 536/23.1, 24.3, 24.33; 422/61
See application file for complete search history.

(56) References Cited

U.S. PATENT DOCUMENTS
2007/0218477 A1 * 9/2007 Thomas ............................. 435/6

FOREIGN PATENT DOCUMENTS
EP          1 020 534       7/2000
JP         2003-325174     11/2003
(Continued)

OTHER PUBLICATIONS
Lizardi, et al. "Mutation detection and single-molecule counting using isothermal rolling-circle amplification," *Nature Genetics*, 19:225-232 (1998).
(Continued)

*Primary Examiner* — Jezia Riley
(74) *Attorney, Agent, or Firm* — Marshall, Gerstein & Borun LLP (57) ABSTRACT

Disclosed is a nucleic acid amplification method which is based on a new principle and enables to amplify a nucleic acid having a specific nucleotide sequence in a simple manner, within a short time and with efficiency. The nucleic acid amplification method comprises the steps of: (a) conducting a DNA polymerase chain reaction by using, as a template, DNA comprising a nucleotide sequence to be amplified and using a primer pair having a nucleotide sequence complementary to the nucleotide sequence to be amplified, thereby producing a linear DNA fragment; and (b) conducting a chain-substituting DNA polymerase chain reaction in a chaining manner by using cyclic single-stranded DNA comprising the same nucleotide sequence as that of at least one of the primer pair as a template and employing the 3'-terminus of the linear DNA fragment produced in step (a) as the replication origin.

10 Claims, 6 Drawing Sheets

FIRST STEP

(i) TARGET GENE (ii) LINEAR DNA FRAGMENT SERVING AS ORIGIN OF REPLICATION IN 2ND STEP

PRIMER

ELONGATION REACTION BY ENZYME

FOREIGN PATENT DOCUMENTS

| | | |
|---|---|---|
| JP | 2005-508599 | 4/2005 |
| JP | 2005-278465 | 10/2005 |
| WO | WO-92/01813 | 2/1992 |
| WO | WO-00/28082 | 5/2000 |
| WO | WO-02/44339 | 6/2002 |

OTHER PUBLICATIONS

Reagin, et al., "TempliPhi: A sequencing template preparation procedure that eliminates overnight cultures and DNA purification," *Jr. of Biomolecular Techniques*, 14:143-148 (2003).

Dean, et al., "Rapid amplification of plasmid and phage DNA using Phi 29 NDA polymerase and multiply-primed rolling circle amplification," *Genome Research*, 11:1095-1099 (2001).

Valasek, et al., "The power of real-time PCR," *Advances in Physiology Education*, 29:151-159 (2005).

International Search Report and Written Opinion for PCT/JP2007/066979 dated Dec. 25, 2007.

Ladner et al., Multiplex detection of hotspot mutations by rolling circle-enabled universal microarrays.*Nature*, 81(8): 1079-86 (2001).

Supplementary European Search Report, EP-07 80 6455, dated May 21, 2010.

\* cited by examiner

FIG. 2

SECOND STEP

FURTHER DNA POLYMERASE ELONGATION REACTION OF
PEELED-OFF DNA STRAND WITH PRIMER OR CIRCULAR
SINGLE-STRANDED DNA

M : MARKER
① : EXPERIMENT 1 IN TABLE 3
② : EXPERIMENT 2 IN TABLE 3
③ : EXPERIMENT 3 IN TABLE 3

A: COMPLEMENTARY PRIMER −
B: COMPLEMENTARY PRIMER +

FIG. 8

A : MARKER
B : COMPLEMENTARY PRIMER −
C : COMPLEMENTARY PRIMER +

NUCLEIC ACID AMPLIFICATION METHOD

TECHNICAL FIELD

The present invention relates to a nucleic acid amplification method, especially to a nucleic acid amplification method using a combination of specific primers and a circular single-stranded DNA, a method for detecting whether or not a target gene is present by the using the above method, and a detection kit to be used for the above method.

BACKGROUND ART

Currently, in various fields including research institutes, medical facilities, inspection agencies, and others, a large number of analytical and detection methods based on a specific base sequence of a target gene are employed. For example, in the case of analyzing and detecting the presence of: a pathogenic microorganism or a minute creature such as a pathogen or allergens including fungus, ticks, and the like; virus; pollen; or the like included in a sample (body fluid or cell fragment) derived from a biological body, such as human and animals, or a sample derived from the environment, methods for detecting a specific base sequence of a target gene included in such detection targets have been used. These methods for detecting nucleic acids (DNA, RNA) can be performed in a shorter period of time and at a higher sensitivity than methods for detecting a protein. Furthermore, even if the amount of nucleic acid originally included in a sample is below a detection limit, the nucleic acid can be amplified relatively easily and specifically using a cell-free system. With these advantages, by using a method for amplifying a nucleic acid or in combination with a method for amplifying a nucleic acid, many methods for detecting a specific base sequence of a target gene have been developed.

Currently, as a nucleic acid amplification technique which are most commonly used, a PCR method is cited in which a cycle of template denaturation, primer annealing to the template, and a DNA polymerase elongation reaction is performed several tens of times by use of a temperature cycle so as to amplify a nucleic acid in a region sandwiched by a primer pair. However, in a method for amplifying a nucleic acid by use of the temperature cycle, an instrument for controlling the temperature cycle (thermal cycler or the like) is expensive and also it is required to examine and set an optimal temperature cycle for nucleic acid amplification.

Therefore, in recent years, a nucleic acid amplification method has been studied in which a DNA polymerase elongation reaction is carried out under a constant temperature condition without using a temperature cycle. A representative example of such a method is a LAMP (Loop-Mediated Isothermal Amplification) method (Patent Document 1). In the LAMP method, four primers are designed for six regions on a target gene so that a 3' end of a DNA strand to be synthesized always forms a loop and serves as an origin of replication of the next DNA amplification reaction, and a nucleic acid molecule of the target gene is amplified.

Furthermore, in Patent Document 2, described is a method in which a linear DNA molecule having, at the 5' end and 3' end, base sequences respectively complementary to two non-continuous regions adjacent to each other in a target gene and having a linker region not complementary to the target gene is designed as a probe, the probe is hybridized to the target gene to form a loop, the juxtaposed 5' end and 3' end are connected by a ligase so as to be circularized, and the base sequence of the circularized probe is amplified by using a primer complementary to the linker region.

However, these existing methods still have problems in terms of cost, design and operation of a detection method, and detection sensitivity; therefore, a new nucleic acid amplification method and a detection method which fully meet these problems is needed.

Patent Document 1: International Patent Publication No. WO 2000/28082
Patent Document 2: Japanese Patent Translation Publication 2005-508599

DISCLOSURE OF THE INVENTION

Problems to be Solved by the Invention

An object of the present invention is to provide a nucleic acid amplification method based on a novel principle in which a nucleic acid having a specific base sequence can be efficiently amplified easily and in a short period of time.

Furthermore, an object of the present invention is to provide a highly-sensitive detection method which enables rapid and clear detection of the presence of a target gene in a sample by using the amplification method.

Moreover, a further object of the present invention is to provide a nucleic acid amplification kit and a detection kit which include a combination of specific primers and a circular single-stranded DNA useful for these methods.

Moreover, a further object of the present invention is to provide a method for manufacturing the circular single-stranded DNA from a single-stranded DNA fragment easily and at a high yield.

Means for Solving the Problems

The inventor of the present invention has discovered that it is possible to efficiently amplify a nucleic acid of a specific base sequence by performing a series of DNA polymerase elongation reaction on a template nucleic acid molecule having a specific base sequence with the use of a combination of primers having a base sequence complementary to the base sequence and a circular single-stranded DNA comprising the same base sequence as the primer in a easy and short-time operation without requiring cyclic temperature control.

Furthermore, the inventor has also discovered that it is possible to rapidly and highly sensitively detect whether or not a target gene is present in a sample, especially, whether or not a microorganism such as an allergen, a virus or a pathogen is present in a sample derived from a biological body or an environment.

These methods and kits useful for these methods are specifically as follows.

A nucleic acid amplification method of the present invention is characterized by comprising:
(a) obtaining a linear DNA fragment by performing a DNA polymerase elongation reaction by using a DNA comprising a base sequence to be amplified as a template and a primer pair having a base sequence complementary to the base sequence; and
(b) performing a series of strand displacement-type DNA polymerase elongation reaction on a circular single-stranded DNA comprising a base sequence identical to at least one of the primer pair as a template and a 3' end of the linear DNA fragment obtained in (a) as an origin of replication.
(a) and (b) are carried out at a temperature at which a strand displacement-type DNA polymerase to be used retains its activity; however, preferably, (a) and (b) are carried out under a same temperature condition.

Furthermore, preferably, the DNA comprising a base sequence to be amplified contains a DNA strand obtained by reverse transcription using RNA as a template.

A kit useful for a nucleic acid amplification method of the present invention is a nucleic acid amplification kit including:
(i) a primer pair having a base sequence complementary to a base sequence to be amplified;
(ii) a circular single-stranded DNA comprising a base sequence identical to at least one of the primer pair;
(iii) a strand displacement-type DNA polymerase; and
(iv) dNTP.

A method for detecting a double-stranded target nucleic acid molecule of the present invention includes:
(a) adding a primer pair having a base sequence complementary to a target base sequence of a target nucleic acid molecule, a circular single-stranded DNA comprising a base sequence identical to at least one of the primer pair, a strand displacement-type DNA polymerase, and dNTP to a sample to be subjected to detection, and performing an enzymatic reaction at a temperature at which the strand displacement-type DNA polymerase retains its activity;
(b) checking whether or not a nucleic acid is amplified in the sample subjected to the enzymatic reaction; and,
(c) in the case where a nucleic acid is amplified, determining that a double-stranded target nucleic acid molecule is present in the sample subjected to detection.

A method for detecting a single-stranded target nucleic acid molecule of the present invention includes:
(a) adding a primer having a base sequence complementary to a target base sequence of a target nucleic acid molecule, a primer having a target base sequence of a region different from a region of the target base sequence of the target nucleic acid molecule, a circular single-stranded DNA including a base sequence identical to at least one of these primers, a reverse transcriptase, a strand displacement-type DNA polymerase, and dNTP to a sample to be subjected to detection, and performing an enzymatic reaction at a temperature at which the strand displacement-type DNA polymerase retains its activity;
(b) checking whether or not a nucleic acid is amplified in the sample subjected to the enzymatic reaction; and,
(d) in the case where a nucleic acid is amplified, determining that a single-stranded target nucleic acid molecule is present in the sample subjected to detection.

A kit useful for a method for detecting a double-stranded target nucleic acid molecule of the present invention is a double-stranded target nucleic acid molecule detection kit including:
(i) a primer pair having a base sequence complementary to a target base sequence of a double-stranded target nucleic acid molecule;
(ii) a circular single-stranded DNA comprising a base sequence identical to at least one of the primer pair;
(iii) a strand displacement-type DNA polymerase; and
(iv) dNTP.

A kit useful for a method for detecting a single-stranded target nucleic acid molecule of the present invention is a single-stranded target nucleic acid molecule detection kit including:
(i) a primer having a base sequence complementary to a target base sequence of a single-stranded target nucleic acid molecule;
(ii) a primer having a target base sequence in a region different from a region of the target base sequence of the target nucleic acid molecule;
(iii) a circular single-stranded DNA including a base sequence identical to at least one of the primers of (i) and (ii);
(iv) a strand displacement-type DNA polymerase; and
(v) dNTP.

Preferably, the detection kit further includes (iv) a reverse transcriptase.

The present invention also provides a manufacturing method of a circular single-stranded DNA which is a manufacturing method including the steps of:
a) preparing a reaction mixture comprising a linear single-stranded DNA, an adapter polynucleotide having sequences located adjacent to each other which are respectively complementary to a 5' end region and a 3' end region of the linear single-stranded DNA, and a thermostable ligase;
b) binding the linear single-stranded DNA and the complementary sequence of the adapter polynucleotide so as to arrange the 5' end and 3' end of the linear single-stranded DNA adjacent to each other;
c) connecting the 5' end and 3' end of the linear single-stranded DNA; and
d) dissociating the single-stranded DNA which has been circularized from the adapter polynucleotide.

EFFECTS OF THE INVENTION

The present invention provides a novel and effective nucleic acid amplification method.

The present invention also provides a simple and rapid detection method for detecting whether or not a target gene is present by the use of the nucleic acid amplification method. By using the detection method, it is possible to rapidly and clearly detect a target gene specific to a pathogenic microorganism, a virus, or the like in an easy operation.

The present invention further provides a combination of primers and a circular single-stranded DNA, which is useful for these methods.

Furthermore, the present invention provides a method for manufacturing a circular single-stranded DNA by using a thermostable DNA ligase, and the present invention enables high-yield synthesis of a circular single-stranded DNA from a linear single-stranded DNA by repeatedly performing a ligation reaction in a single enzymatic reaction mixture.

BEST MODES FOR CARRYING OUT THE INVENTION

In a nucleic acid amplification method of the present invention, amplification products which have various chain lengths and include a base sequence to be amplified in a single or multiple repetitions can be obtained by a DNA polymerase elongation reaction, and a further DNA polymerase elongation reaction in which these amplification products serves as a template or an origin of replication proceeds in a chain reaction so that the base sequence to be amplified can be efficiently amplified.

A template DNA including a base sequence to be amplified (also referred to as "a target base sequence" in the present description) of the present invention is a single-stranded or double-stranded linear or circular DNA, and the base sequence to be amplified included in the template DNA is a base sequence in a specific region in the template DNA. Furthermore, the method of the present invention can be carried out by using cDNA, which is obtained by synthesizing a base sequence complementary to RNA molecules using a reverse transcriptase, as a template DNA. In this case, the base sequence to be amplified of the present invention is a base sequence in which uracil (U) in the RNA molecule is substituted by thymine (T).

A primer pair used in the amplification method of the present invention includes a base sequence complementary to a target base sequence to be amplified in the template DNA, and may be anything with which a region sandwiched by the primer pair (including the base sequences of the primer pair) on the basis of the template DNA can be obtained as a linear DNA fragment. Accordingly, in the case where the template DNA is a double-stranded DNA, primers of the primer pair each have target base sequences on respective strands. In the case where the template DNA is a single-stranded DNA, one primer of the primer pair has a target base sequence in a region different from a base sequence to be amplified which is present on the template DNA strand.

The method of the present invention can be carried out by using at least one primer pair. In the case of using multiple primer pairs, there is no upper limit to the number; however, for example, a nested design may be adopted. For example, the number is in a range from 1 to 5 pairs, preferably in a range from 1 to 3 pairs, more preferably in a range from 2 to 3 pairs, and especially preferably 2 pairs.

It is preferable that the individual primers do not include a sequence identical or complementary to the other primer in a pair or a primer of other primer pair.

A relative distance (number of bases) between regions to which primers in a pair bind is not particularly limited as long as the reaction of the present invention can proceed. However, it is preferable that the relative distance between the regions to which primers of a primer pair located innermost is smaller, and also that the relative distance between the regions to which a primer pair located outside thereof and an adjacent inside primer pair is smaller. The relative distance (number of bases) is preferably in a range from 0 b to 1 kb, and more preferably in a range from 0 to 100 b.

As for a primer to be used in the present invention, it is not particularly limited as long as the primer can form a complementary double strand with the template DNA; however, the primer is preferably in a range from 8 to 40 mer, and more preferably in a range from 16 to 25 mer. Furthermore, as for properties generally taken into consideration in primer design, such as GC content and secondary structure forming propensity of a template DNA (target base sequence) or the primer, they are also within a range of common technical knowledge of a person skilled in the art. Such a primer design and synthesis can be carried out by using a technique, such as a design program commonly used in the present technical field.

In the case where cDNA obtained by synthesizing a base sequence in an RNA molecule by using a reverse transcriptase is used as a template DNA, a primer pair can also be designed in a similar manner as described above depending on whether the RNA molecule is double stranded or single stranded.

A circular single-stranded DNA used in the method of the present invention includes at least one base sequence identical to at least one of primers of the primer pair, and the base sequence identical to at least one of the primers has a base sequence complementary to a base sequence to be amplified.

The circular single-stranded DNA may be designed so as to include a base sequence identical to one primer in multiple repetitions at constant intervals, or to include base sequences respectively identical to multiple primers in a single or multiple repetitions. In the case of using multiple primer pairs, a base sequence included in a circular single-stranded DNA is preferably identical to at least one of base sequences of the primer pair used innermost.

In the circular single-stranded DNA, a base sequence in a region other than a base sequence identical to a primer is not particularly limited as long as the reaction of the present invention proceeds specifically; however, it is preferably smaller. Furthermore, in the case of using a strand displacement-type DNA polymerase which has no 3' to 5' exonuclease activity, it is preferable to add one thymine (T) to the 5' end of the base sequence identical to a primer.

A chain length of the circular single-stranded DNA is not particularly limited as long as the reaction of the present invention proceeds specifically; however, it is preferably in a range from 16 b to 10 kb, and more preferably in a range from 20 to 100 b. Design and synthesis of such a circular single-stranded DNA can be carried out by using a technique, such as a design program commonly used in the present technical field. Furthermore, a circular single-stranded DNA can also be manufactured by a manufacturing method of a circular single-stranded DNA, which will be described later.

A DNA polymerase used in the method of the present invention has a strand displacement-type 5' to 3' DNA polymerase activity, and preferably allows correct synthesis of a complementary strand of a base pair. Furthermore, the DNA polymerase may have 3'-5' exonuclease activity, but preferably has no 3'-5' exonuclease activity, and preferably has no 5'-3' exonuclease activity. An optimum temperature of a DNA polymerase is preferable in a range from 50 to 90° C., and more preferably in a range from 60 to 72° C. As such a DNA polymerase, for example, Bst DNA polymerase large fragment derived from *Bacillus stearothermophilus*, Deep Vent$_R$(R) (exo-) DNA polymerase derived from a bacterium belonging to the genus *Pyrococcus* (manufactured by New England Biolabs Incorporation), Herculase(R) II Fusion DNA polymerase (manufactured by STRATAGENE), Vent$_R$(R) (exo-) DNA polymerase derived from a strain of the genus *Thermococcus*, Therminator™ DNA polymerase, Therminator™ II DNA polymerase (manufactured by New England Biolabs Incorporation), KOD Dash DNA polymerase (manufactured by Toyobo, Co., Ltd), and the like are available by itself or in a kit. Two kinds or more DNA polymerases can be used together as long as they do not interfere with the enzymatic activity of the other.

For an elongation reaction by DNA polymerase, a buffer generally used for nucleic acid amplification (including salts, such as Tris-HCl, KCl, $(NH_4)_2SO_4$, and $MgSO_4$), for example, one having an optimized composition provided with a DNA polymerase to be used, may be used.

By adding a template DNA, a primer pair of the present invention, a circular single-stranded DNA of the present invention, a strand displacement-type DNA polymerase, and four kinds of deoxyribonucleoside triphosphates (dNTP: dATP, dCTP, dGTP, and dTTP) which serve as a substrate to an appropriate buffer described above, and maintaining this reaction solution at a temperature at which the strand displacement-type DNA polymerase retains its enzymatic activity, for example, at a temperature in a range from 50 to 90° C., preferably in a range from 60 to 72° C., it is possible to efficiently amplify a nucleic acid in a single operation in a single container without applying temperature cycle control. In the meantime, in the case of using multiple primer pairs, it is possible to set a reaction temperature condition of the present invention to a lower condition, for example, in a range from 30 to 50° C. A temperature condition for a DNA polymerase elongation reaction depends on a temperature at which a strand displacement-type DNA polymerase to be used retains its activity. It is not necessarily required to maintain a uniform temperature (constant temperature) throughout the amplification reaction as long as the temperature is within a temperature range in which a strand displacement-type DNA polymerase to be used retains its enzymatic activity; however, it is preferable to maintain a uniform temperature (constant temperature) throughout the amplification reaction (under a constant temperature condition).

Amplification of a nucleic acid can be checked by a precipitation of magnesium pyrophosphate generated in a reaction solution when a nucleic acid is amplified in a DNA polymerase elongation reaction (International Patent Publication No. WO 2001/083817). Alternatively, it is also possible to check the amplification of a nucleic acid from the presence of fluorescence or the intensity thereof by using a nucleic acid staining fluorescent dye, for example, ethidium bromide, SYBR green (manufactured by CAMBREX), or the like, which is commonly used in the present technical field in accordance with a common procedure.

Next, by using drawings, an aspect of a nucleic acid amplification method of the present invention will be specifically described.

Figure 1:
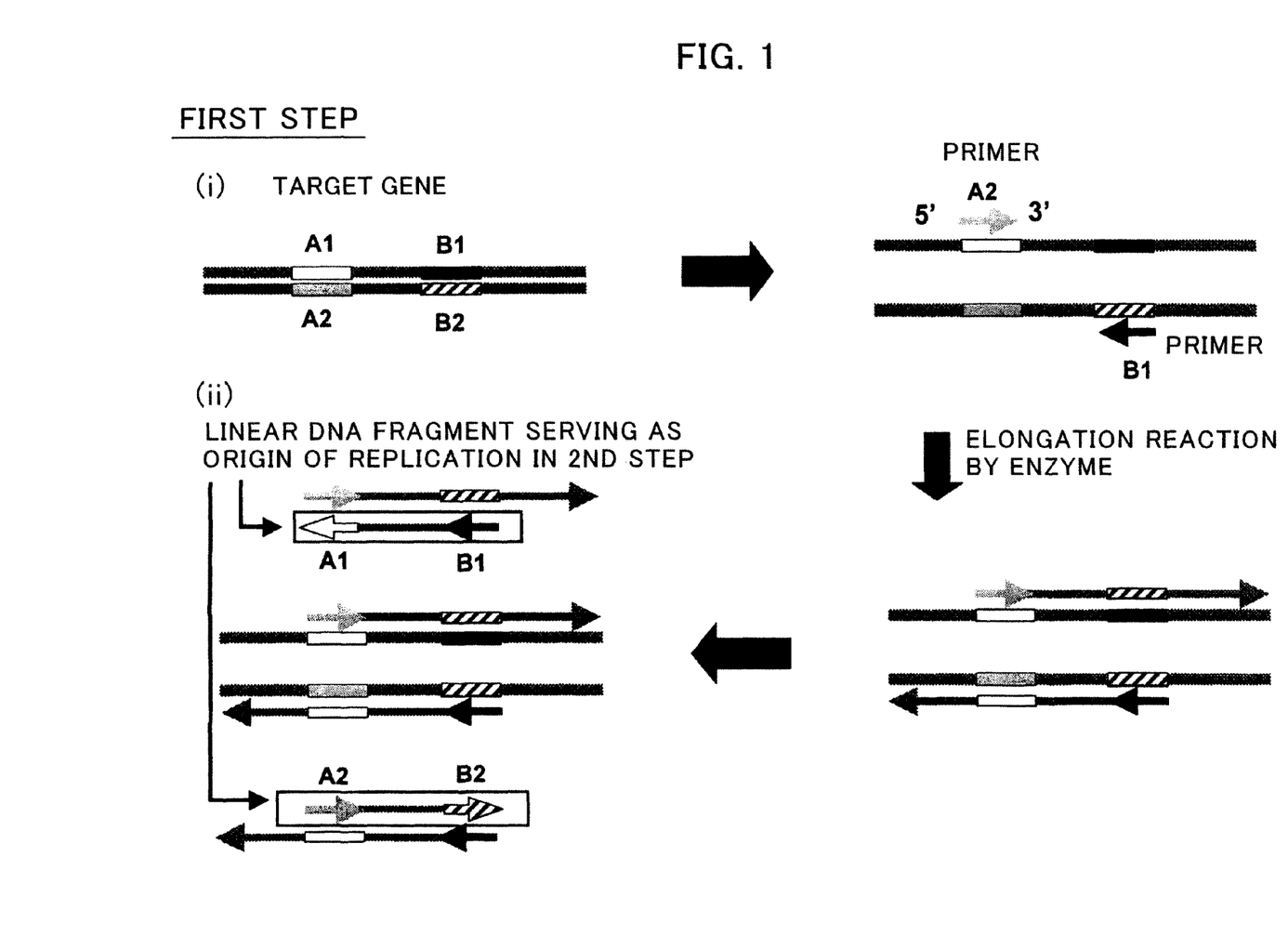
FIG. 1 illustrates a principle (first stage) of a nucleic acid amplification method of the present invention.

Firstly, in a first step, a linear DNA fragment can be obtained by a DNA polymerase elongation reaction with a template DNA comprising a specific base sequence to be amplified and a primer pair (FIG. 1).

In the case where two regions A and B having a specific base sequence in a double-stranded template DNA are to be amplified, respective sequences of the regions on one strand are defined as A1 and B1, and respective sequences on the other strand are defined as A2 and B2. Among the primer pair, one primer is designed so as to have a base sequence complementary to A1, that is, a base sequence of A2, and the other primer is designed to have a base sequence complementary to B2, that is, B1 (FIG. 1, (i)).

By the DNA polymerase elongation reaction with the primer pair and the template DNA, a combination of a linear DNA fragment having, at the 5' end thereof, a base sequence identical to A2 and, at the 3' end thereof, a base sequence identical to B2 and a linear DNA fragment having, at the 5' end thereof, a base sequence identical to B1 and, at the 3' end thereof, a base sequence identical to A1 can be obtained. The obtained linear DNA fragment serves as an origin of replication when a second step is initiated (FIG. 1, (ii)).

Figure 2:
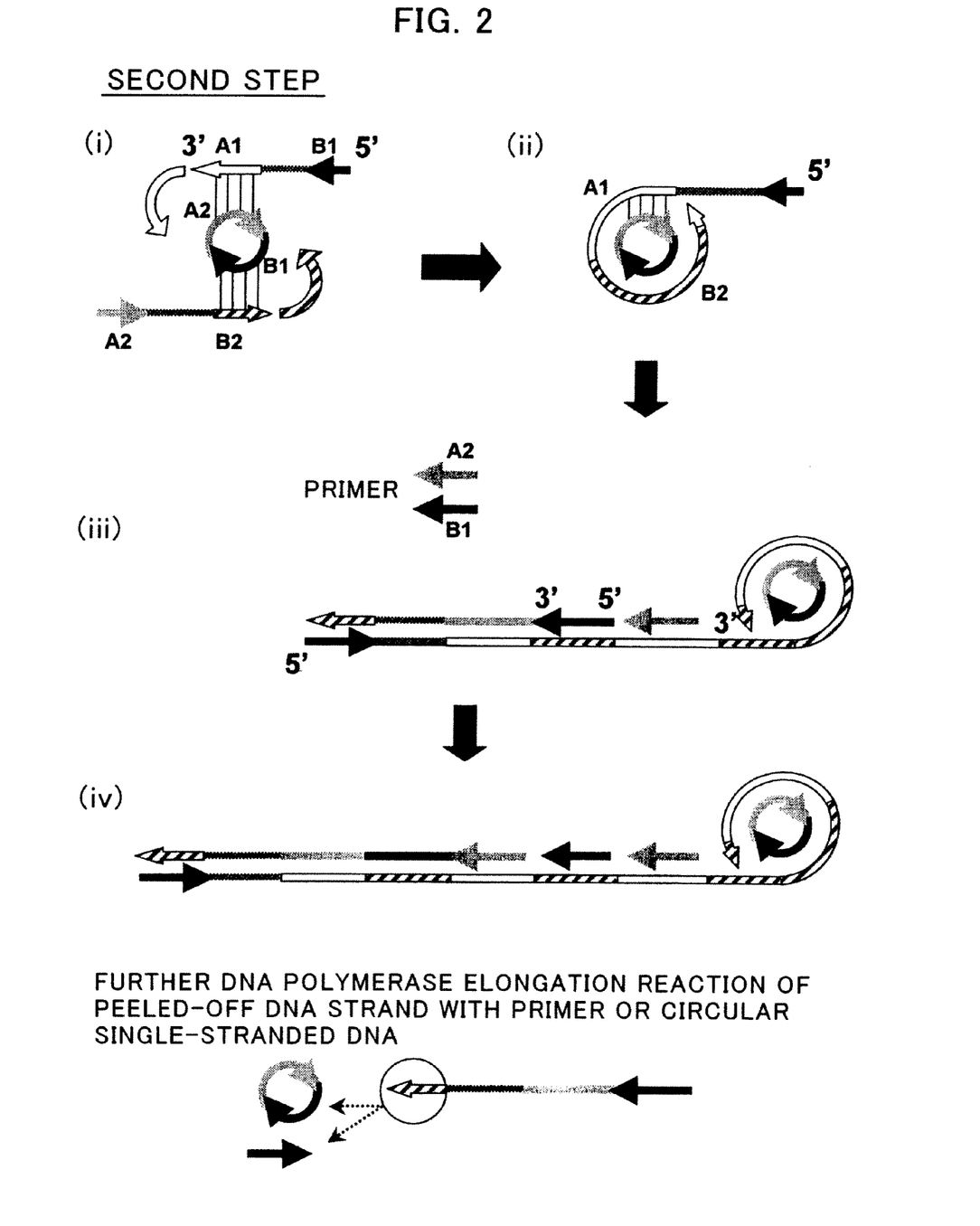
FIG. 2 illustrates a principle (second stage) of the nucleic acid amplification method of the present invention.
Figure 3:
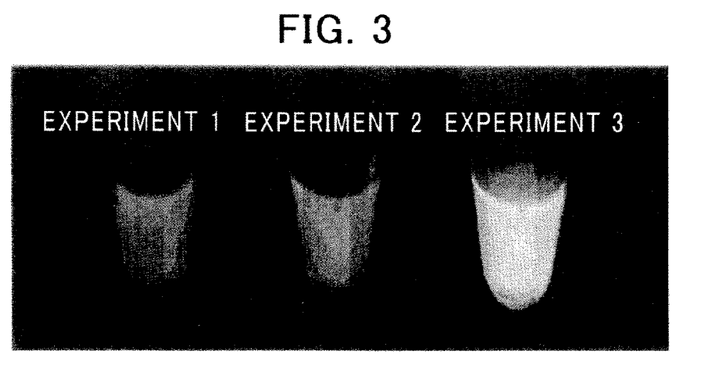
FIG. 3 shows experimental results (Experiment 1 to Experiment 3) in Table 3.
Figure 4:
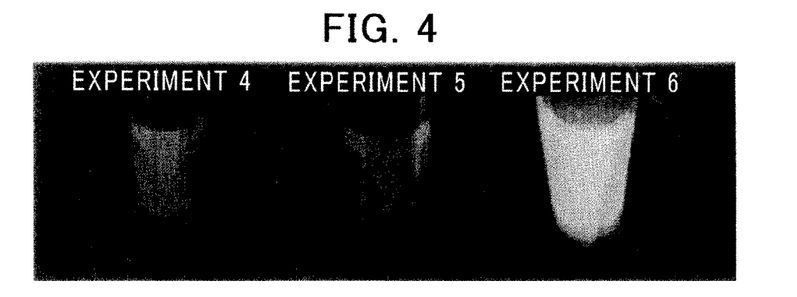
FIG. 4 shows experimental results (Experiment 4 to Experiment 6) in Table 3.
Figure 5:
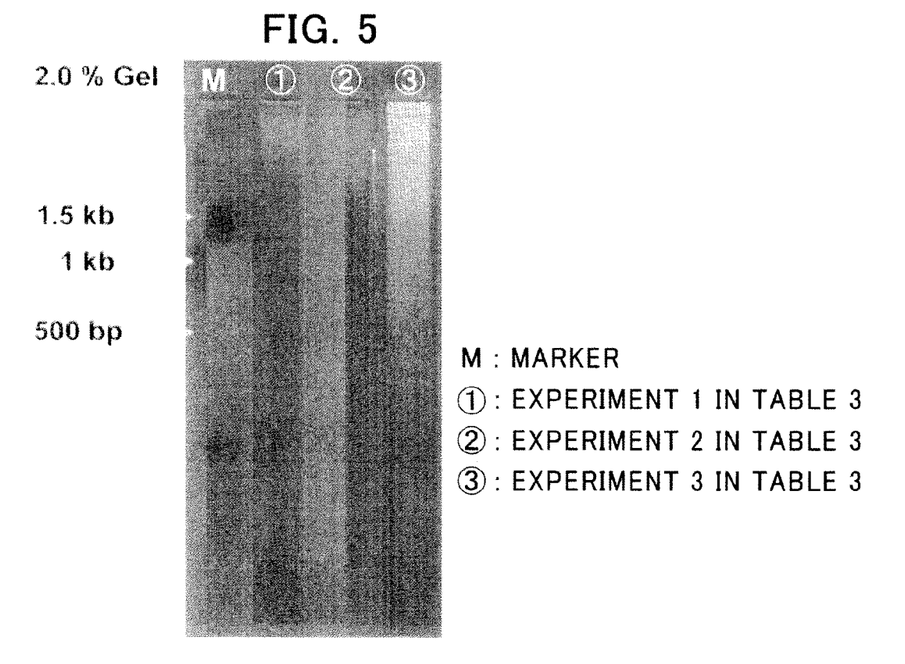
FIG. 5 shows results of electrophoresis of samples in Experiment 1 to Experiment 3 in Table 3.

A circular single-stranded DNA which is to serve as a template in a second step is designed so as to include a base sequence identical to at least one of the primer pair (A2 and/or B1) (FIG. 2, (i)). In FIG. 2, a circular single-stranded DNA comprising base sequences respectively identical to A2 and B1 is illustrated. Since the obtained linear DNA fragment has, at the 3' end thereof, a base sequence complementary to the primer pair (A1 or B2) as described above, a 3' end region (A1, B2) of the linear DNA fragment anneals to a base sequence (A2, B1) region of the circular single-stranded DNA identical to the primer pair and serves as an origin of replication. Accordingly, a DNA polymerase elongation reaction occurs with the circular single-stranded DNA as a template (FIG. 2, (i)). The synthesized DNA strand is elongated in a rolling circle pattern while being peeled off by the strand displacement-type DNA polymerase (FIG. 2, (ii)). A primer in the reaction solution anneals to the DNA strand having been peeled off and elongated and serves as an origin of replication, and then a DNA polymerase elongation reaction occurs (FIG. 2, (iii)). The DNA strand synthesized with the primer as an origin of replication and peeled off anneals to a primer or a circular single-stranded DNA in the reaction solution, and a DNA polymerase reaction occurs (FIG. 2, (iv)).

The process in the first step and the process in the second step which are described above proceed simultaneously in parallel once after a linear DNA fragment which triggers the initiation of the second step is synthesized. Then, a series of amplification reactions proceeds as described above, and, as a result, DNA strands which include a specific base sequence to be amplified in a single or multiple repetitions and have various chain lengths are synthesized.

Another aspect of the present invention is a detection method of a target gene based on the principle of the above-described nucleic acid amplification method. The detection method can be carried out in various scenes in various industries in accordance with an object of detection, an origin of a sample to be subjected to detection, a target gene, and the like.

A sample from which a target gene is to be detected, for example, may be prepared from a body fluid or a tissue fragment derived from human or other animals, may be prepared from soil, ocean water, or a plant derived from the environment, or may be a beverage, a food item, or a medical product manufactured and processed in a factory. These can be used as a sample to be subjected to detection by the detection method of the present invention after being prepared as a nucleic acid (DNA, RNA) extract directly or if needed by an appropriate operation. Such sample preparation can be carried out in accordance with a standard technique which is used in a general nucleic acid detection method.

A target gene may be specific to a microorganism (bacterium, fungus, or the like), an allergen (for example, tick, pollen, or the like), or a virus, or may be a wild-type or a mutant-type gene in a genome of human or other animals.

In the present detection method, "a template DNA" and "a base sequence to be amplified" in the above-described nucleic acid amplification method are replaced by "a target nucleic acid molecule (that is, target gene)" and "a target base sequence in a target gene" of the present detection method, respectively, and the present detection method utilizes the fact that, in the case where a target nucleic acid molecule (that is, a target gene) is present in a sample, a nucleic acid of the target base sequence in the target gene can be amplified on the basis of the same principle as in the above-described nucleic acid amplification method.

In the case of detecting a double-stranded target nucleic acid molecule, a target nucleic acid molecule can be detected by:

(a) adding a primer pair having a base sequence complementary to a target base sequence of a target nucleic acid molecule, a circular single-stranded DNA comprising a base sequence identical to at least one of primers of the primer pair, a strand displacement-type DNA polymerase, and dNTP to a sample to be subjected to detection, and performing an enzymatic reaction at a temperature at which the strand displacement-type DNA polymerase retains its activity;

(b) checking whether or not a nucleic acid is amplified in the sample subjected to the enzymatic reaction; and, (c) in the case where a nucleic acid is amplified, determining that a double-stranded target nucleic acid molecule is present in the sample subjected to detection.

In the case of detecting a single-stranded target nucleic acid molecule, by respectively replacing "a primer pair having a base sequence complementary to a target base pair of a target nucleic acid" and "a circular single-stranded DNA comprising a base sequence identical to at least one of primers of the primer pair" by "a combination of a primer having a base sequence complementary to a target base sequence of a target nucleic acid molecule and a primer having a target base sequence in a region different from a region of the target base sequence of the target nucleic acid" and "a circular single-stranded DNA comprising a base sequence identical to at least one of the primers," a single-stranded target nucleic acid molecule can be detected by performing the same operation as in the case where a target nucleic acid molecule is double stranded.

In the case where a target nucleic acid molecule is RNA, in the step of the enzymatic reaction in (a) described above, similarly to the above-described nucleic acid amplification method, an enzymatic reaction is performed by further adding a reverse transcriptase (RNA-dependent DNA polymerase) to a sample so as to check whether or not a nucleic acid can be amplified with a cDNA strand, which is synthesized from an RNA molecule in the sample, as a template, and, in the case where a nucleic acid has been amplified, the presence of a target RNA molecule can be detected by determining that the target RNA molecule is present.

Amplification of a nucleic acid can be checked in a similar manner as described above by using the presence of precipitation or fluorescence as an indicator with the use of a precipitation of magnesium pyrophosphate or by using a nucleic acid staining fluorescent dye or the like commonly used in the present technical field. Furthermore, by using an amount of magnesium pyrophosphate generated or intensity of fluorescence as an indicator, an amount of nucleic acid of a target gene present in a sample to be subjected to detection can also be compared.

As described above, by using the present detection method, even if there is only a minute amount of nucleic acid of a target gene present in a sample, it is possible to efficiently amplify and detect a specific base sequence in the target gene in a single operation within a single reaction container. The present detection method may be performed in a reaction container, for example, a micro tube, a microwell plate, a microchip, or the like, and a technique, such as HTS (High-Throughput Screening), may be adopted.

In a manufacturing method of a circular single-stranded DNA of the present invention, in step (a), a reaction mixture comprising a linear single-stranded DNA, an adapter polynucleotide having a sequence complementary to the linear single-stranded DNA, and a thermostable ligase is prepared.

The type and the number of bases of the linear single-stranded DNA used for circularization are not particularly limited, and may be a genomic sequence isolated from an actual cell or a polynucleotide sequence artificially synthesized. It is generally only required that a sufficient number of bases for circularization be provided, and the number is, for example, at least 20 bases, preferably in a range from 20 to 200 bases, and more preferably in a range from 30 to 80 bases.

Although depending on a thermostable DNA ligase to be used, in the case where a linear single-stranded DNA to be used for circularization is an artificially synthesized polynucleotide, it is preferable that the 5' end thereof be phosphorylated, but does not necessarily have to be phosphorylated. Furthermore, it is desirable that no other modification be applied.

In the meantime, the adapter polynucleotide has complementary sequences respectively to a 5' end region and a 3' end region of the linear single-stranded DNA, and, in particular, has complementary sequences, which are located adjacent to each other, respectively to a 5' end region and a 3' end region of the linear single-stranded DNA. In the present invention, "5' end region" and "3' end region" refer to a region including an endmost base of the 5' end and the 3' end of the linear single stranded DNA, respectively, and the length of the region can be generally set to a value necessary for annealing of a polynucleotide by a person skilled in the art. For example, a value in a range from 5 to 20 bases is appropriate, and a total of the 5' end region and the 3' end region is preferably in a range from approximately 15 to approximately 30 bases when a adapter polynucleotide synthesis is taken into consideration.

In the manufacturing method of a circular single-stranded DNA of the present invention, "complementary sequences (to a 5' end region and a 3' end region)" are preferably sequences completely complementary to a sequence in regions at the 5' end and the 3' end of the linear single-stranded DNA, respectively. However, as long as annealing to the linear single-stranded DNA is possible, a mismatched base pair may be included. The number of such base pairs depends on the reaction conditions and the length of the whole region, and may be 1, 2, 3, or the like in each region or may be in a range from approximately 1% to approximately 50% of the whole bases in each region. Note that, as understood by a person skilled in the art, in order to efficiently perform ligation, it is preferable that bases at the 5' end and the 3' end at which ligation is actually performed by a ligase in circularization form base pairs with their respective bases of the adapter.

Figure 6:
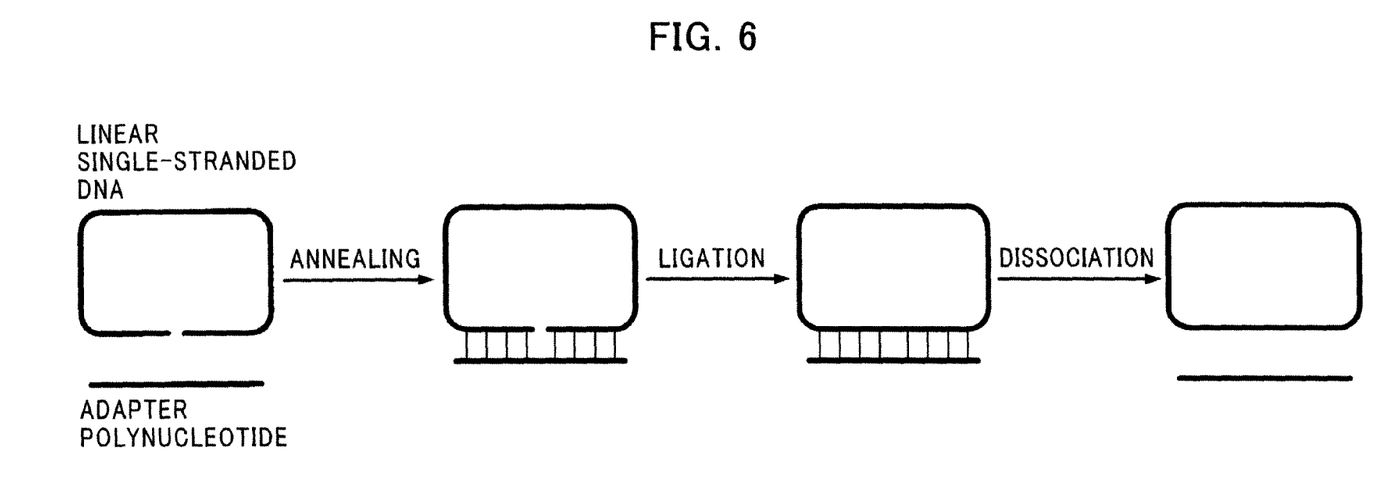
FIG. 6 illustrates an outline of manufacture of a circularized single-stranded DNA by a method of the present invention.

The adapter polynucleotide of the present invention has, as described above, sequences, which are located adjacent to each other, respectively complementary to the 5' end region and the 3' end region. Here, "being located adjacent to each other" means that the 5' end complementary sequence is continuous with the following 3' end complementary sequence from the 5' side without having any base therebetween. Such an adapter polynucleotide can arrange, as illustrated in FIG. 6, the linear single-stranded DNA in a circular form by annealing to the linear single-stranded DNA.

In the manufacturing method of a circular single-stranded DNA of the present invention, a thermostable DNA ligase is used for a ligation reaction for circularization of a linear single-stranded DNA. A thermostable DNA ligase is an enzyme which ligates the 5' end and the 3' end of respective adjacent DNA strands by a phosphodiester bond, and indicates an enzyme which does not substantially lose its activity even at a temperature at which a double-stranded DNA is dissociated to single-stranded DNAs (DNA dissociation temperature), for example, at a temperature in a range from 80 to 100° C., preferably 90 to 95° C. For example, a ligase is cited which retains 30% or more, preferably 50% or more of its enzymatic activity even after being exposed at a temperature in a range from 95 to 100° C., which is generally used as a dissociation temperature, for approximately 30 minutes to approximately 1 hour. A ligase which is commercially available as a ligase appropriate for the use in an LCR reaction is generally recognized as a member of "thermostable DNA ligase." A thermostable DNA ligase is generally isolated from a hyperthermophilic bacterium, such as *Pyrococcus furiosus*, *Aeropyrum pernix*, and *Thermococcus* sp., or an extremely thermophilic bacterium, such as *Thermus aquaticus*, and one which has been subjected to recombination in order to further increase the thermostability may be used for the method of the present invention. More specifically, (Pfu DNA ligase manufactured by Stratagene, Ampligase DNA ligase manufactured by Epicentre, thermostable DNA ligase manufactured by Wako Pure Chemical Industries, Ltd., 9° $N^{th}$ DNA ligase manufactured by New England Biolabs, Taq DNA ligase) and the like can be cited.

In the manufacturing method of a circular single-stranded DNA of the present invention, the reaction mixture prepared in step a) contains the above-described linear single-stranded DNA, the above-described adapter polynucleotide, and the above-described thermostable DNA ligase. Their concentrations and abundance ratios can be accordingly determined based on the common technical knowledge of the field. The concentration of the linear single-stranded DNA is, for example, in a range from 1 to 100 μmol/l, preferably in a range from 20 to 80 µmol/l, and more preferably in a range from 40 to 60 µmol/l, while the concentration of the adapter polynucleotide is, for example, in a range from 0.05 to 50 µmol/l, preferably in a range from 1 to 40 µmol/l, and more preferably in a range from 3 to 12 µmol/l. However, their concentrations are not limited to these ranges. Furthermore, a preferable molar ratio of the linear single-stranded DNA to the adapter polynucleotide changes depending on the number of repetitions of ligation reaction, which will be described later; however, the preferable molar ratio is in a range, for example, from 100:1 to 1:5, preferably in a range from 50:1 to 1:1, and more preferably in a range from 20:1 to 4:1.

Here, in the manufacturing method of a circular single-stranded DNA of the present invention, the adopter polynucleotide can be reused after being dissociated from a circularized single-stranded DNA. Accordingly, even in the case where the adapter polynucleotide is present at a ratio lower than the linear single-stranded DNA (for example, at a molar ratio of 20:1, as indicated above) in the reaction mixture, it is possible to efficiently manufacture a circular single-stranded DNA.

An amount of the thermostable DNA ligase to be added, in the case where, for example, a commercially-available ligase is used, may be determined to a preferable value on the basis of the concentration or the amount of DNA in the reaction mixture in accordance with an instruction of a manufacturer.

Furthermore, the reaction mixture prepared in step a) may further contain various substances necessary for a ligation reaction. Generally, the composition of a reaction buffer is determined by the type of ligase to be used, and, for example, Tris-HCl (pH 7.5), KCl, $MgCl_2$, ATP, NAD(P), DTT and the like, may be contained at an appropriate concentration. In reality, it is sufficient to use a reaction buffer provided with a commercially-available ligase in accordance with an instruction of a manufacturer.

After preparing the reaction mixture comprising a linear single-stranded DNA, an adapter polynucleotide, and a thermostable DNA ligase in the above-described step a), a circular single-stranded DNA is manufactured by performing binding (annealing) between the linear single-stranded DNA and the adapter polynucleotide, circularization by a ligation reaction, and isolation of a circularized single-stranded DNA from the adapter polynucleotide by heat denaturation in steps b) to d), respectively (refer to FIG. 6).

More specifically, in step b), the 5' end and the 3' end of the linear single-stranded DNA are arranged adjacent to each other by binding the linear single-stranded DNA and the complementary sequence of the adapter polynucleotide. Binding (annealing) between the linear single-stranded DNA and the adapter polynucleotide is performed by placing the reaction mixture at an appropriate temperature, and the temperature is in a range, for example, from 55 to 65° C., and preferably 60° C. However, as understood by a person skilled in the art, the appropriate value changes depending on the length or $T_m$ value of the adapter polynucleotide; therefore, the appropriate value can be adjusted accordingly. The reaction time can also be arbitrary set based on the relationship with the length of the polynucleotide or the reaction temperature, and the reaction time is in a range, for example, from 1 second to 3 minutes, preferably in a range from 5 seconds to 1 minute, and more preferably 10 seconds. However, it is sufficient if the reaction mixture has substantially reached a set temperature, and it is also possible to employ a longer time setting.

In step b), the linear single-stranded DNA is bent so as to have a structure in which the 5' end and the 3' end are located next or close to each other when the linear single-stranded DNA and the complementary sequence of the adopter polynucleotide are bound; therefore, it is possible to efficiently perform circularization (ligation reaction) in the following step c).

In step c), the 5' end and the 3' end of the linear single-stranded DNA are ligated. More specifically, by placing the reaction mixture at an appropriate temperature for a certain period of time, the DNA ligase contained in the reaction mixture acts to ligate the 5' end and the 3' end of the linear single-stranded DNA. The reaction temperature is preferably set to an optimum temperature of a thermostable DNA ligase to be used; however, the reaction temperature can be freely set within a temperature range in which the ligase retains its activity. For example, in the case of using a thermostable DNA ligase manufactured by Wako Pure Chemical Industries, Ltd., the temperature is set in a range from 60 to 90° C., preferably to 70° C. An appropriate reaction time depends on the kind of ligase or an amount of enzyme, and is, for example, in a range from 5 to 30 minutes, and preferably 10 minutes.

In step d), a circularized single-stranded DNA and the adapter polynucleotide are dissociated. More specifically, by placing the reaction mixture at a dissociation temperature (high temperature) of DNA of the reaction mixture, the circular single-stranded DNA and the adapter polynucleotide, which are bound to each other at a point when step c) is completed, are dissociated. The reaction temperature may be simply a commonly-used DNA dissociation temperature, and is set in a range, for example, from 90 to 100° C., and preferably in a range from 93 to 98° C., and set to, for example, 95° C. Meanwhile, the reaction time can be set in a range, for example, from 1 second to 1 minute, preferably in a range from 5 to 30 seconds, and more preferably to 10 seconds. In this step, the adopter polynucleotide is back to the original single-stranded state. Accordingly, it is possible to reuse the adapter polynucleotide for binding with a single-stranded DNA which has not been circularized when the operation goes back again to step b) as described later.

Preferably, a series of operations of steps b) to d) (hereinafter, also referred to as a cycle) in the manufacturing method of a circular single-stranded DNA of the present invention is repeatedly performed. By repeating the cycle in steps b) to d) so as to circularize the linear single-stranded DNA one after another while repeatedly using the adapter polynucleotide, it is possible to manufacture a circularized single-stranded DNA at a high yield.

The number of repetition is, for example, at least twice, preferably 10 times or more, and more preferably 25 times or more, and an appropriate number of times can be determined by a person skilled in the art in consideration of depletion of the linear single-stranded DNA, a decrease in the ligase activity, a required yield of circularized single-stranded DNA, or the like.

Here, the manufacturing method of a circular single-stranded DNA of the present invention also includes variously modified or improved methods on the basis of the common technical knowledge of the present technical field. For example, in the case of repeatedly performing steps b) to d), it is only necessary that individual cycles in the middle, except for the first and the last, include steps b), c), and d), and these steps be performed in this order. A person skilled in the art easily understands that a means for appropriately manufacturing a circular single-stranded DNA can be adopted especially in the first and last cycles.

For example, generally, it is preferable to prevent non-specific annealing by raising the temperature of the reaction mixture to a dissociation temperature immediately after the reaction is initiated. In the present invention, a treatment is performed, for example, at 95° C. for 2 minutes. Alternatively, after the reaction mixture is placed at a ligation temperature in step c) in the last cycle, the reaction mixture may be treated at a dissociation condition (for example, 98° C. for 2 minutes) different from that in other cycles so as to dissociate the circular single-stranded DNA and the adapter polynucleotide. Furthermore, the reaction may be terminated by rapidly cooling the reaction mixture to 4° C. thereafter.

In addition, change in the settings of the temperature and time for each cycle or change regarding a configuration that steps b) and c) are performed at the same time under the same condition may be possible.

The present invention will be concretely described hereinafter with reference to Examples.

EXAMPLES

Chemicals without a company name denoted thereafter are manufactured by Wako Pure Chemical Industries, Ltd. Furthermore, unless otherwise specifically stated, a solvent is water.
(TE Buffer Composition)
4 mmol/l Tris-HCl (tris-hydroxymethyl-aminomethane) hydrochloric acid
1 mmol/l ethylene diamine tetraacetic acid, disodium salt, dihydrate (EDTA)
Adjusted to pH 8.0
(1.2% TAE Electrophoresis Gel)
1.2% agarose
4 mmol/l Tris-HCl
1 mmol/l EDTA
1 mmol/l acetic acid
(2.0% TAE Electrophoresis Gel)
2.0% agarose
4 mmol/l Tris-HCl
1 mmol/l EDTA
1 mmol/l acetic acid Example 1

[Target Preparation Method]

Enzyme products and kit products described below are used in accordance with the respective manuals unless otherwise specifically stated.

After being treated with a restriction enzyme DraI (Takara Bio Inc.), pUC19 (Takara Bio Inc.) was subjected to electrophoresis (100 V, 50 minutes) by using 1.2% TAE electrophoresis gel in Mupid-ex (Advance Co., Ltd.), which is an electrophoresis chamber.

Thereafter, staining with a nucleic acid staining reagent SYBR GreenI (manufactured by CAMBREX) was performed, a target DNA fragment (approximately 2 kb) was cut out from the gel and subjected to collection using a DNA extraction kit, NucleoSpin Extract Kit (MACHEREY-NAGEL Inc.), and a target preparation solution (10 mmol/l) was obtained.

[Synthesis of a Circular Single-Stranded DNA]

Primers used for synthesis of a circular single-stranded DNA are shown in Table 1. The 5' end of 43C is phosphorylated, and Bind has been subjected to cartridge purification (manufactured by Invitrogen Co.).

TABLE 1

Primer sequences used for synthesis of circular single-stranded DNA

| Name | Sequence (5' to 3') |
|---|---|
| 43C | ACAGCTATGACTCGACGTTGTAAAACGACGGCTCACACAGGAA |
| Bind | GTCATAGCTGTTTCCTGTGTG |

The two primers in Table 1 (43C: 75 nmol/l, Bind: 1.6 nmol/l) were mixed with a thermostable DNA ligation enzyme (thermostable ligase), and an enzymatic reaction was performed according to a temperature profile described below.

| | |
|---|---|
| 95° C., 2 minutes | Step 1 |
| 95° C., 10 seconds | Step 2 |
| 60° C., 10 seconds | Step 3 |
| 25 cycles of steps 2 to 4 | |
| 70° C., 10 minutes | Step 4 |
| 98° C., 2 minutes | Step 5 |
| 4° C., ∞ | Step 6 |

After the reaction is completed, Gen Toru Kun (Takara Bio Inc.) was added, and ethanol precipitation was performed. Thereafter, the obtained DNA pellet was washed with 75% ethanol twice and 99.5% ethanol once, dried at 65° C., and dissolved in 30 µl of ultrapure water.

The solution was added with Exonuclease I (Takara Bio Inc.), subjected to a reaction at 37° C. for 60 minutes, and then subjected to ethanol precipitation. The obtained DNA pellet was washed with 75% ethanol twice and 99.5% ethanol once, dried at 65° C., and dissolved in 30 µl of TE buffer to obtain a circular single-stranded DNA preparation solution.

[Specific Gene Amplification]

Primers used for gene detection are shown in Table 2. Both were subjected to HPLC purification (manufactured by Invitrogen Co.).

TABLE 2

Primer sequences used for gene detection

| Name | Sequence (5' to 3') |
|---|---|
| Forward-in | CGACGTTGTAAAACGACGGC |
| Reverse-in | CACACAGGAAACAGCTATGAC |

In a gene detection reaction, the followings were used.

Enzyme: Bst DNA polymerase (manufactured by New England Biolabs Incorporation) 4 U/25 µl Target: target preparation solution 0.5 µl/25 µl λ genome: λ genome (Takara Bio Inc.) 0.5 ng/µl

| (Reaction buffer composition) | |
|---|---|
| ¹⁄₁₀ volume | a buffer provided with Bst DNA polymerase |
| 1 µmol/l | primers in Table 2 (Forward-in, Reverse-in) |
| 0.5 mmol/l each | dNTP |
| 0.02 µg/ml | circular single-stranded DNA preparation solution |

The reagents were mixed under the conditions in Table 3, incubated at 95° C. for 5 minutes, rapidly cooled down to 4° C., added with the enzyme, and then incubated at 63° C. for 60 minutes.

[Check Method for DNA Amplification]

A nucleic acid staining reagent SYBR GreenI was diluted to 1/10, 1 µl thereof was added to 25 µl of the sample, and observation was performed at a wavelength of 302 nm with a highly-sensitive filter. The results are shown in Table 3 and FIG. 1.

TABLE 3

DNA amplification results

|  | Enzyme | Target | λ genome | Reaction buffer | Nucleic acid amplification |
|---|---|---|---|---|---|
| Experiment 1 | x | ○ | x | ○ | − |
| Experiment 2 | ○ | x | x | ○ | − |
| Experiment 3 | ○ | ○ | x | ○ | + |
| Experiment 4 | x | ○ | ○ | ○ | − |
| Experiment 5 | ○ | x | ○ | ○ | − |
| Experiment 6 | ○ | ○ | ○ | ○ | + |

According to the results of Experiments 1 to 6 shown above, rapid nucleic acid amplification was observed in the samples comprising the enzyme+the target (Experiment 3 and Experiment 6). On the other hand, in the samples comprising the enzyme and no target (Experiment 2 and Experiment 5), no nucleic acid amplification was observed. Furthermore, no nucleic acid amplification was observed even in the sample comprising DNA other than the target sequence (Experiment 5). Accordingly, it was observed that the sequence was specifically recognized. Note that, no nucleic acid amplification was performed for the samples comprising no enzyme (Experiment 1 and Experiment 4).

Example 2

[Specific Gene Amplification]

Specific gene amplification was performed by using a circular single-stranded DNA preparation solution prepared in a similar manner as that in Example 1.

Primers used for gene detection are shown in Table 4. All were subjected to HPLC purification (manufactured by Invitrogen Co.).

TABLE 4

Primer sequences used for gene detection

| Name | Sequence (5' to 3') |
|---|---|
| Forward-in | CGACGTTGTAAAACGACGGC |
| Forward-out | ACGCCAGGGTTTTCCCAGTC |
| Reverse-in | CACACAGGAAACAGCTATGAC |
| Reverse-out | TGGAATTGTGAGCGGATAAC |

In a gene detection reaction, the followings were used.
Enzyme: Bst DNA polymerase (manufactured by New England Biolabs Incorporation) 4 U/25 μl
Target: target preparation solution 0.5 μl/25 μl
λ genome: λ genome (Takara Bio Inc.) 0.5 ng/μl

| (Reaction buffer composition) | |
|---|---|
| 1/10 volume | a buffer provided with Bst DNA polymerase |
| 1 μmol/l | primers in Table 4 (Forward-in, Reverse-in) |
| 0.2 μmol/l | primers in Table 4 (Forward-out, Reverse-out) |
| 0.5 mmol/l each | dNTP |
| 1 μmol/l | circular single-stranded DNA preparation solution |
| 5% | Dimethylsulfoxide |

The reagents were mixed under conditions in Table 5, incubated at 95° C. for 5 minutes, rapidly cooled down to 4° C., added with the enzyme, and then incubated at 63° C. for 60 minutes.

[Check Method for DNA Amplification]

A nucleic acid staining reagent SYBR Greenl was diluted to 1/10, 1 μl thereof was added to 25 μl of the sample, and observation was performed at a wavelength of 302 nm with a highly-sensitive filter. The results are shown in Table 5.

TABLE 5

DNA amplification results

|  | Enzyme | Target | λ genome | Reaction buffer | Presence of fluorescence |
|---|---|---|---|---|---|
| Experiment 7 | x | ○ | x | ○ | − |
| Experiment 8 | ○ | x | x | ○ | − |
| Experiment 9 | ○ | ○ | x | ○ | + |
| Experiment 10 | x | ○ | ○ | ○ | − |
| Experiment 11 | ○ | x | ○ | ○ | − |
| Experiment 12 | ○ | ○ | ○ | ○ | + |

According to the results in Experiments 7 to 12 shown above, rapid nucleic acid amplification was observed in the samples comprising the enzyme+the target (Experiment 9 and Experiment 12). On the other hand, in the samples comprising the enzyme and no target (Experiment 8 and Experiment 11), no nucleic acid amplification was observed. Furthermore, no nucleic acid amplification was observed even in the sample comprising DNA other than the target sequence (Experiment 11). Accordingly, the result showed that the sequence was specifically recognized. Note that, no nucleic acid amplification was performed for the samples comprising no enzyme (Experiment 7 and Experiment 10).

As in the above-described Examples, it was shown that the present invention makes it possible to specifically recognize a nucleic acid sequence and to perform rapid nucleic acid amplification.

Example 3

[Synthesis of Circular Single-Stranded DNA]

The two kinds of polynucleotides in Table 1 (43C: 60 μmol/l, Bind: 3 μmol/l) and a recombinant thermostable DNA ligase manufactured by Wako Pure Chemical Industries, Ltd. (1.25 μl) were mixed to a total of 25 μl, and a reaction was performed under conditions shown below. In addition, a reaction buffer provided with the thermostable DNA ligase was used. The final compositions in the mixed solution are the buffer (2.5 μl/25 μl) provided with the thermostable ligase (1.25 μl/25 μl) and the two kinds of polynucleotides in Table 1 (43C: 60 μmol/l, Bind: 3 μmol/l).

The mixture was subjected to an enzymatic reaction at the same temperature condition as in [Synthesis of circular single-stranded DNA] in Example 1, subjected to ethanol precipitation in the same manner, and dissolved in 30 μl of TE buffer to obtain a circular single-stranded DNA preparation solution.

[Check of Synthesis of Circular Single-Stranded DNA]

Synthesis of a circular single-stranded DNA was checked by a polymerase reaction.

| Reaction mixture composition | |
|---|---|
| 0.02 μg/ml | circular single-stranded DNA preparation solution |
| 1.6 nmol/l | primers in Table 2 (Forward-in and Reverse-in) |
| 4 U/ 25 μl | Bst DNA polymerase (New England Biolabs Incorporation) |
| 1.6 nmol/l | primer in Table 1 (Bind) |

(The reaction buffer was used in accordance with an instruction of a manufacturer of Bst DNA polymerase)

The reaction mixture described above was prepared, and then incubated at 63° C. for 60 minutes. In the meantime, a control mixture which does not include Bind primer was prepared, and then incubated as well.

This reaction is to replicate DNA in the 3' direction by the Bind polynucleotide, which annealed to the circular single-stranded DNA, serving as a primer and to further amplify DNA by F and R primers with the replicated DNA used as a template.

[Detection]

A nucleic acid staining reagent SYBR GreenI (Takara Bio Inc.) was diluted to 1/10, 1 μl thereof was added to 25 μl of the sample, and observation was performed at a wavelength of 302 nm with a highly-sensitive filter.

Furthermore, electrophoresis (100 V, 60 minutes) was performed using a 2.0% TAE electrophoresis gel and Mupid-ex (Advance Co., Ltd.), which is an electrophoresis chamber, and, thereafter, the gel was stained with a nucleic acid staining reagent SYBR GreenI and observed at a wavelength of 254 nm with a highly-sensitive filter.

Figure 7:
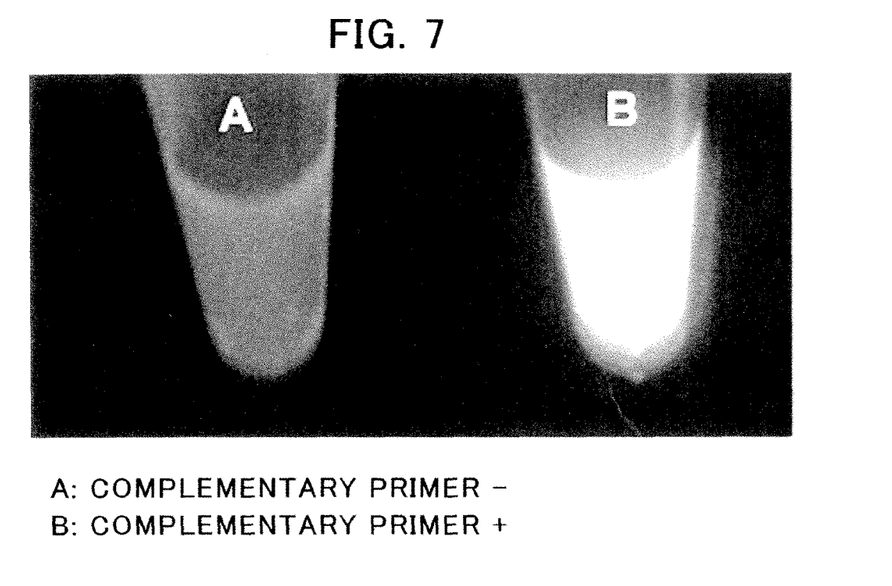
FIG. 7 shows a photograph in which a circular single strand is detected by using SYBR GreenI. A is a control sample in which a polymerase reaction was performed without adding a primer, and B is a sample in which a normal synthesis reaction was performed.
Figure 8:
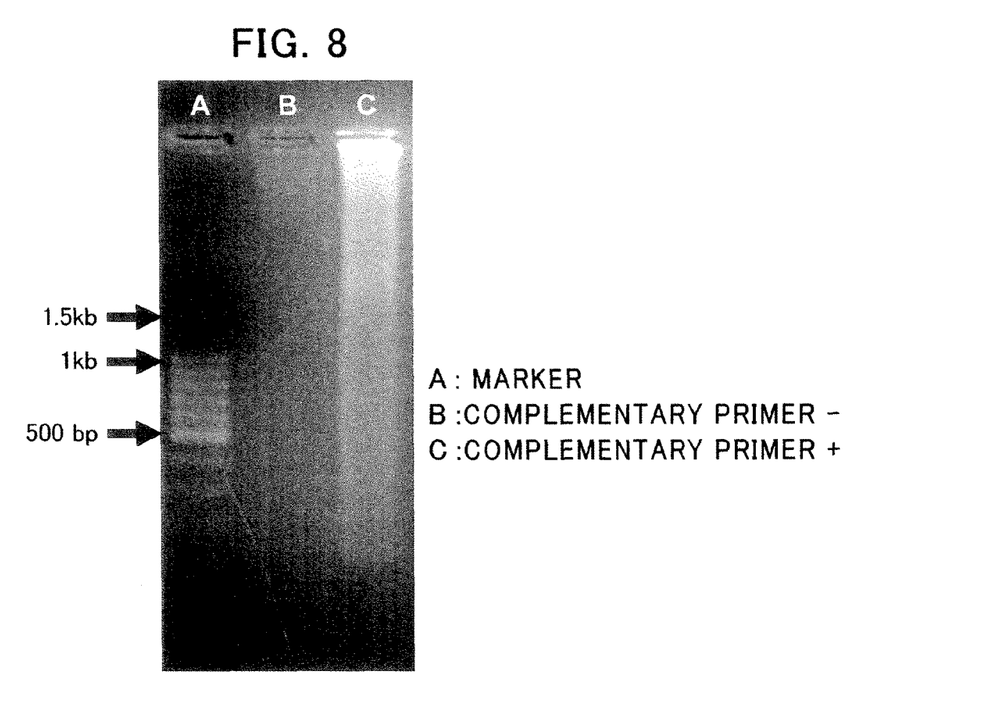
FIG. 8 shows a photograph of a gel in which a circular single strand was detected by electrophoresis.

The results are shown in Table 6, FIG. 7, and FIG. 8.

TABLE 6

Results of circular single strand synthesis check

| | Primer (Bind) | Reaction buffer | Nucleic acid amplification |
|---|---|---|---|
| A | − | ○ | x |
| B | + | ○ | ○ |

FIG. 7 and FIG. 8 show that a long-chain DNA was synthesized; therefore, it was found out that a circular single-stranded DNA was synthesized. Furthermore, at the same time, it was also found out that it is possible to decompose those other than a circular single strand by the treatment with Exonuclease I.

[Comparison of Concentration of Circular Single-Stranded DNA by a Repeating Reaction of Ligation Reaction]

In the same method as described in [Synthesis of circular single-stranded DNA] above, a ligation reaction was repeatedly performed, and the concentration of circular single-stranded DNA generated was compared.

The concentration of a linear single-stranded DNA and an adapter polynucleotide to be added to the reaction mixture was prepared so that the concentrations are 60 μmol/l of 43C and 3 μmol/l of Bind.

C: no ligase
D: one cycle of (2) to (4)
E: 25 cycles of (2) to (4)

After the reaction, Gen Toru Kun (Takara Bio Inc.) was added, and ethanol precipitation was performed. Thereafter, the obtained pellet was washed with 75% ethanol twice and 99.5% ethanol once, dried at 65° C., and dissolved in 30 μl of ultrapure water.

Figure 9:
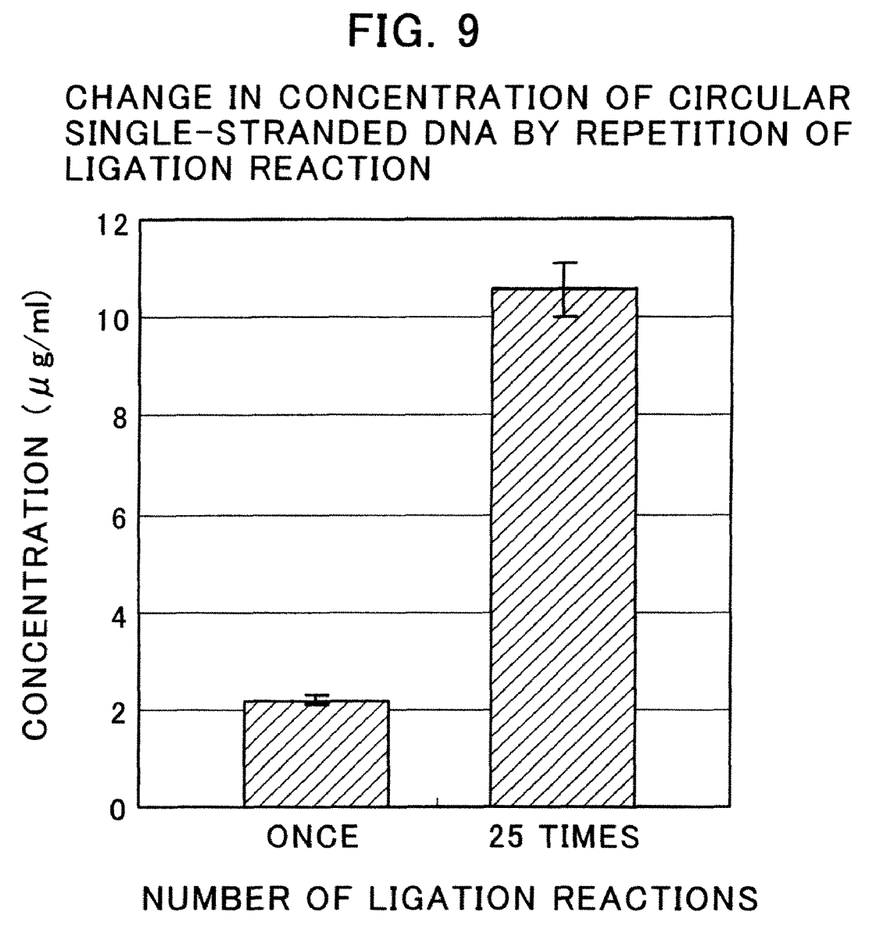
FIG. 9 shows a graph in which concentrations of circular single strand synthesis in the cases where a ligation reaction was performed once and where a ligation reaction was repeated 25 times were compared.

After the dissolution, the obtained solution was added with Exonuclease I (Takara Bio Inc.), subjected to a reaction at 37° C. for 60 minutes, added with Gen Toru Kun, and then subjected to ethanol precipitation. Thereafter, the obtained pellet was washed with 75% ethanol twice and 99.5% ethanol once, dried at 65° C., dissolved in 25 μl of TE buffer, and the subjected to detection of concentration by absorbance (260 nm) (FIG. 9). C which was performed without adding the ligase was set as a zero point.

According to FIG. 9, it was found out that a circular single-stranded DNA was manufactured at a high yield by performing a ligation cycle repeatedly using the method of the present invention.

The invention claimed is:

1. A nucleic acid amplification method comprising:
   (a) obtaining a linear DNA fragment by performing a DNA polymerase elongation reaction by using a template DNA comprising a target base sequence and a primer pair having a base sequence complementary to said target base sequence; and
   (b) performing a strand displacement-type DNA polymerase elongation reaction on a circular single-stranded DNA comprising a base sequence identical to at least one of the primer pair as a template and a 3' end of the linear DNA fragment obtained in (a) as an origin of replication.

2. The method according to claim 1, comprising performing (a) and (b) at a same temperature condition.

3. The method according to claim 1, wherein the template DNA comprising the target base sequence includes a DNA strand obtained by reverse transcription using RNA as a template.

4. A nucleic acid amplification kit, comprising:
   (i) a primer pair having a target base sequence complementary to a base sequence;
   (ii) a circular single-stranded DNA comprising a base sequence identical to the primer pair in a same molecule;
   (iii) a strand displacement-type DNA polymerase; and
   (iv) dNTP.

5. A method for detecting a double-stranded target nucleic acid molecule, comprising:
   (a) adding a primer pair having a base sequence complementary to a target base sequence of a target nucleic acid molecule, a circular single-stranded DNA comprising a base sequence identical to at least one of the primer pair, a strand displacement-type DNA polymerase, and dNTP to a sample to be subjected to detection, and performing an enzymatic reaction at a temperature at which the strand displacement-type DNA polymerase retains its activity;
   (b) checking whether or not a nucleic acid is amplified in the sample subjected to the enzymatic reaction; and, (c) in the case where a nucleic acid is amplified, determining that a double-stranded target nucleic acid molecule is present in the sample subjected to detection.

6. A method for detecting a single-stranded target nucleic acid molecule, comprising:
(a) adding a primer having a base sequence complementary to a target base sequence of a target nucleic acid molecule, a primer having a target base sequence of a region different from a region of the target base sequence of the target nucleic acid molecule, a circular single-stranded DNA including a base sequence identical to at least one of these primers, a strand displacement-type DNA polymerase, and dNTP to a sample to be subjected to detection, and performing an enzymatic reaction at a temperature at which the strand displacement-type DNA polymerase retains its activity;
(b) checking whether or not a nucleic acid is amplified in the sample subjected to the enzymatic reaction; and, (d) in the case where a nucleic acid is amplified, determining that a single-stranded target nucleic acid molecule is present in the sample subjected to detection.

7. A double-stranded target nucleic acid molecule detection kit, comprising:
(i) a primer pair having a base sequence complementary to a target base sequence of a double-stranded target nucleic acid molecule;
(ii) a circular single-stranded DNA comprising a base sequence identical to at least one of the primer pair;
(iii) a strand displacement-type DNA polymerase; and
(iv) dNTP.

8. A single-stranded target nucleic acid molecule detection kit, comprising:
(i) a primer having a base sequence complementary to a target base sequence of a single-stranded target nucleic acid molecule;
(ii) a primer having a target base sequence in a region different from a region of the target base sequence of the target nucleic acid molecule;
(iii) a circular single-stranded DNA including a base sequence identical to at least one of the primers of (i) and (ii);
(iv) a strand displacement-type DNA polymerase; and
(v) dNTP.

9. The detection kit according to claim 8, further comprising (vi) a reverse transcriptase.

10. The method according to claim 2, wherein the template DNA comprising the target base sequence includes a DNA strand obtained by reverse transcription using RNA as a template.

* * * * *

SEQUENCE LISTING

<160> NUMBER OF SEQ ID NOS: 6

<210> SEQ ID NO 1
<211> LENGTH: 43
<212> TYPE: DNA
<213> ORGANISM: Artificial
<220> FEATURE:
<223> OTHER INFORMATION: designed polynucleotide

<400> SEQUENCE: 1
acagctatga ctcgacgttg taaaacgacg gctcacacag gaa           43

<210> SEQ ID NO 2
<211> LENGTH: 21
<212> TYPE: DNA
<213> ORGANISM: Artificial

-continued

```
<220> FEATURE:
<223> OTHER INFORMATION: designed polynucleotide

<400> SEQUENCE: 2
gtcatagctg tttcctgtgt g                                      21

<210> SEQ ID NO 3
<211> LENGTH: 20
<212> TYPE: DNA
<213> ORGANISM: Artificial
<220> FEATURE:
<223> OTHER INFORMATION: designed polynucleotide

<400> SEQUENCE: 3
cgacgttgta aaacgacggc                                        20

<210> SEQ ID NO 4
<211> LENGTH: 21
<212> TYPE: DNA
<213> ORGANISM: Artificial
<220> FEATURE:
<223> OTHER INFORMATION: designed polynucleotide

<400> SEQUENCE: 4
cacacaggaa acagctatga c                                      21

<210> SEQ ID NO 5
<211> LENGTH: 20
<212> TYPE: DNA
<213> ORGANISM: Artificial
<220> FEATURE:
<223> OTHER INFORMATION: designed polynucleotide

<400> SEQUENCE: 5
acgccagggt tttcccagtc                                        20

<210> SEQ ID NO 6
<211> LENGTH: 20
<212> TYPE: DNA
<213> ORGANISM: Artificial
<220> FEATURE:
<223> OTHER INFORMATION: designed polynucleotide

<400> SEQUENCE: 6
tggaattgtg agcggataac                                        20
```